US011931546B2

(12) United States Patent
Tanneberg et al.

(10) Patent No.: US 11,931,546 B2
(45) Date of Patent: Mar. 19, 2024

(54) METHOD FOR CALIBRATING A SYRINGE PUMP, SYRINGE PUMP AND APPARATUSES

(71) Applicant: Fresenius Medical Care Deutschland GmbH, Bad Homburg (DE)

(72) Inventors: Michael Tanneberg, Erfurt (DE); Jochen Siebert, Strahlungen (DE); Ralf Rogmann, Schwebheim (DE); Patrick Dietz, Weichtungen (DE); Jochen Rueckert, Roethlein (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 745 days.

(21) Appl. No.: 17/045,592

(22) PCT Filed: Apr. 4, 2019

(86) PCT No.: PCT/EP2019/058488
§ 371 (c)(1),
(2) Date: Oct. 6, 2020

(87) PCT Pub. No.: WO2019/193089
PCT Pub. Date: Oct. 10, 2019

(65) Prior Publication Data
US 2021/0052808 A1 Feb. 25, 2021

(30) Foreign Application Priority Data
Apr. 6, 2018 (DE) .......................... 102018108203.7

(51) Int. Cl.
*A61M 5/145* (2006.01)
*A61K 31/7016* (2006.01)
(Continued)

(52) U.S. Cl.
CPC ....... *A61M 5/1452* (2013.01); *A61K 31/7016* (2013.01); *A61M 1/16* (2013.01);
(Continued)

(58) Field of Classification Search
CPC ................ A61M 5/142; A61M 5/1452; A61M 5/1456; G16H 40/40; G16G 20/17; G01D 5/16; G01D 5/145
See application file for complete search history.

(56) References Cited

U.S. PATENT DOCUMENTS

| 4,873,655 A | 10/1989 | Kondraske |
| 5,034,004 A | 7/1991 | Crankshaw |
| 5,998,218 A | 12/1999 | Conley et al. |

(Continued)

FOREIGN PATENT DOCUMENTS

| CN | 101185042 | 5/2008 |
| CN | 102764469 | 11/2012 |

(Continued)

OTHER PUBLICATIONS

PCT International Preliminary Report on Patentability in International Appln. No. PCT/EP2019/058488, dated Oct. 15, 2020, 17 pages (with English translation).
PCT International Search Report and Written Opinion in International Appln. No. PCT/EP2019/058488, dated Aug. 7, 2019, 20 pages (with English translation).

*Primary Examiner* — Tiffany Legette
(74) *Attorney, Agent, or Firm* — Fish & Richardson P.C.

(57) ABSTRACT

The present disclosure describes a medical syringe pump and a method for calibrating a medical syringe pump. In some cases the medical syringe pump is configured and/or prepared to execute the method according to the present disclosure, or has been calibrated accordingly. This disclosure also describes a blood treatment apparatus which comprises such syringe pump or is connected to such syringe pump. Furthermore, the present disclosure describes a digital storage medium and/or a computer program product as a computer program.

34 Claims, 4 Drawing Sheets

(51) Int. Cl.
    *A61M 1/16*     (2006.01)
    *A61M 1/28*     (2006.01)
    *A61M 1/34*     (2006.01)
    *G01D 5/14*     (2006.01)
    *G01D 5/16*     (2006.01)
    *G01D 5/32*     (2006.01)
    *G16H 20/17*     (2018.01)
    *G16H 40/40*     (2018.01)

(52) U.S. Cl.
    CPC ................ *A61M 1/28* (2013.01); *A61M 1/34* (2013.01); *A61M 1/3413* (2013.01); *G01D 5/145* (2013.01); *G01D 5/16* (2013.01); *G01D 5/32* (2013.01); *G16H 20/17* (2018.01); *G16H 40/40* (2018.01); *A61M 2205/3317* (2013.01); *A61M 2205/502* (2013.01); *A61M 2205/52* (2013.01); *A61M 2205/70* (2013.01)

(56) References Cited

U.S. PATENT DOCUMENTS

| | | |
|---|---|---|
| 2003/0233069 A1 | 12/2003 | Gillespie, Jr. et al. |
| 2006/0079765 A1 | 4/2006 | Neer et al. |
| 2008/0167615 A1 | 7/2008 | Niehoff |
| 2008/0265807 A1 | 10/2008 | Rose |
| 2014/0197824 A1 | 7/2014 | Gillespie et al. |
| 2014/0243750 A1 | 8/2014 | Larsen et al. |
| 2017/0056581 A1 | 3/2017 | Deak et al. |
| 2017/0067980 A1 | 3/2017 | Thiagarajan et al. |

FOREIGN PATENT DOCUMENTS

| | | |
|---|---|---|
| CN | 103768679 | 5/2014 |
| EP | 3202440 | 8/2017 |
| KR | 101502509 | 3/2015 |
| WO | WO 2006113408 | 10/2006 |
| WO | WO 2016050902 | 4/2016 |
| WO | WO 2016142216 | 9/2016 |
| WO | WO 2017050781 | 3/2017 |

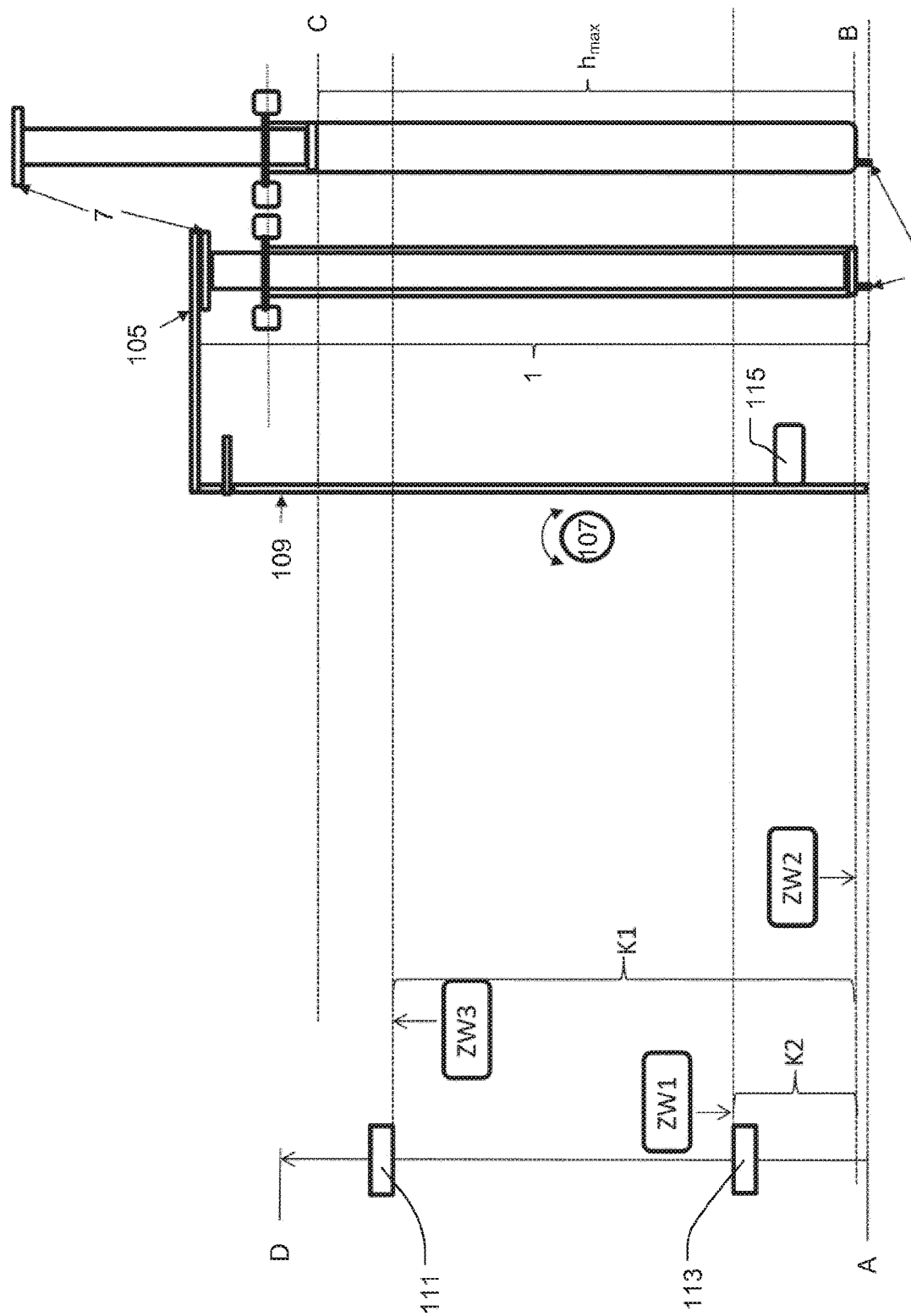

METHOD FOR CALIBRATING A SYRINGE PUMP, SYRINGE PUMP AND APPARATUSES

CROSS-REFERENCE TO RELATED APPLICATIONS

The present application is the national stage entry of International Patent Application No. PCT/EP2019/058488, filed on Apr. 4, 2019, and claims priority to Application No. DE102018108203.7, filed in the Federal Republic of Germany on Apr. 6, 2018, the disclosures of which are expressly incorporated herein in its entirety by reference thereto.

FIELD OF THE INVENTION

The present disclosure relates to a method for calibrating a medical syringe pump. It further relates to a medical syringe pump and to a blood treatment apparatus. The present disclosure further relates to a digital storage medium, a computer program product and a computer program.

BACKGROUND

Syringe pumps are known from practical experience. The associated pump control requires signals which indicate defined positions of the linear movement of the movable or shiftable slide of the syringe pump, by or through which the syringe is emptied. These signals are registered by sensors, which may be, for example, magnet field sensors (e.g. Hall sensors) or optoelectronic sensors (e.g. light barriers). The sensors of this syringe pumps serve for the pump control in order to determine or detect or define the actual position of the slide and hence serving the correct or accurate controlling of the pump motor.

To ensure a correct and precise controlling of the motor, the syringe pump must undergo in advance a complicated calibration process.

SUMMARY

In some embodiments, the present disclosure is directed to a preferably automated or mostly automated, method for calibrating a medical syringe pump. In addition, a medical syringe pump, which is configured and/or prepared for executing such method or which was calibrated by such method, and a blood treatment apparatus are disclosed herein. Furthermore, a suitable digital storage medium, a suitable computer program product and a suitable computer program for executing the method are disclosed herein.

In all of the following statements, the use of the expression "may be" or "may have" and so on, is to be understood synonymously with "preferably is" or "preferably has," and so on respectively, and is intended to illustrate embodiments according to the present disclosure.

Whenever numerical words are mentioned herein, the person skilled in the art shall recognize or understand them as indications of numerical lower limits. Unless it leads the person skilled in the art to an evident contradiction, the person skilled in the art shall comprehend the specification for example of "one" as encompassing "at least one". This understanding is also equally encompassed by the present disclosure as the interpretation that a numeric word, for example, "one" may alternatively mean "exactly one", wherever this is evidently technically possible for the person skilled in the art. Both are encompassed by the present disclosure and apply herein to all used numerical words.

Herein, when "programmed" or "configured" is mentioned, it is also disclosed that these terms are interchangeable.

The information "top" and "bottom" are herein to be understood in case of doubt by the person skilled in the art as absolute or relative spatial information, which refers to the orientation of the respective element when used as intended.

The method according to the present disclosure for calibrating a medical syringe pump relates to a syringe pump with a syringe receptacle for receiving a syringe, which comprises a syringe cylinder and plunger being movable therein between a first end position and a second end position, wherein the plunger is connected or comprises a plunger rod.

Further, the medical syringe pump to be calibrated comprises a syringe motor and a slide which may be movable by the syringe motor in motor steps being in particular distinguishable from each other or definable against each other. The slide comprises a toggle or pin for receiving a section of the plunger rod of the syringe or for connecting the toggle thereto. This section may be a push plate which is connected to the plunger rod. A section of the slide is arranged to be movable by the slide, e.g. relative to the syringe receptacle, maximally between a first end stop and a second end stop. The slide is configured to be moved in motor steps (these could be microsteps). This occurs longitudinally to the position of syringe being inserted in the syringe pump during use of the latter.

Further, the syringe pump to be calibrated comprises a counting device for counting the number of motor steps by which the slide is moved, e.g. similar to an odometer. The counting device may preferably count back and forth. It may also preferably be set to zero or another start value.

In addition, the syringe pump to be calibrated comprises a first sensor and a second sensor, both of which are arranged along a shifting path of the plunger of the syringe or along a movement path of the slide of the pump. They are optionally configured and/or arranged to be in sensor relationship with the slide or with a section thereof.

Moreover, the syringe pump to be calibrated comprises a control device which is configured to move the slide by following control instructions. These control instructions may, for example, be entered by a user using an input device and/or stored by a storage device and read out from the latter.

For this purpose and possibly for storing the data detected by the sensors or the calculated calibration values, the syringe pump comprises a storage device.

Finally, an input device for entering control instructions and/or other data by the user is also provided.

In some embodiments, the method according to the present disclosure for calibrating the medical syringe pump encompasses one or more of the following steps:

a) The optional input of at least one piece of information about a specific type of the syringe. The input may be made by the input device. It may be stored by the storage device.

b) Moving a section of the slide, in particular at a first speed, in or to a start position or a use position, e.g. a middle position between the first end position and the second end position, in particular in a position between the first and the second sensor, however as long as this position has not been reached yet.

c) Moving the toggle, in particular at a second speed, such that the plunger, when the syringe is inserted in the syringe pump, would reach or come to the first end position or until a predetermined section of the slide, e.g. the permanent magnet, reaches the first end stop. Hereby, when a predetermined section of the slide, e.g. a permanent magnet, reaches or passes by the position of the second sensor, this position is set or determined as a first counting value or is considered equivalent thereto. This is for example the case, precisely when the permanent magnet passes (or reaches the level of) the second sensor exemplarily designed as a Hall sensor, or when a light barrier which corresponds to the second sensor is interrupted by the predetermined section. This first count value may be e.g. a number of motor steps provided by the counting device. Possibly, the first count value is, optionally temporarily, stored. Furthermore, when the plunger or the predetermined section reaches the first end position or when the section of the slide reaches the first end stop then the motor steps, which have been counted by the counting device starting from the position of the second sensor until reaching or having reached the position of the first end position or of the first end stop, are set or determined as a second count value. Also, this value is optionally, e.g. temporarily, stored.

d) Calculating a calibration value of the second sensor based on the first count value and the second count value, e.g. as a difference between, or the sum of, the first count value and the second count value, or as the absolute value therefrom, said calculation being done by a calculation device programmed for this purpose or by the counting device being optionally configured therefor, and storing this calibration value for the second sensor by the storage device.

e) Optionally, the counting device is reset to "0" or to another start value.

f) Moving the toggle or the slide, in particular at the second or at a third speed, towards the second end position.

g) Setting or determining the number of motor steps as third count value which number of motor steps is given or output by the counting device when the predetermined section of the slide has reached the position of the first sensor or has passed by it (e.g. the permanent magnet passing by a Hall sensor, or the passing of a light barrier).

h) Calculating a calibration value of the first sensor based on the third count value and optionally based on at least a further value from the group consisting of the first count value, the second count value and the calibration value of the second sensor, e.g. as the difference between the second and the third count value or as the absolute value of the third count value, said calculation being done by e.g. a therefor suitable calculation device or by the counting device, and storing this calibration value for the first sensor by the storage device.

Calculating the calibration values may in the simplest case be a simple reading out of the count value, e.g. when the respective start value was "0".

The first speed may be between 100 µs/microstep and 1000 µs/microstep, preferable 500 µs/microstep. The second speed may be between 1000 µs/microstep and 10000 µs/microstep, preferably 5000 µs/microstep. Alternatively, the second speed may be between 1000 µs/microstep and 2000 µs/microstep, in particular 1400 µs/microstep. The third speed may be between 10000 µs/microstep and 50000 µs/microstep, preferably 20000 µs/microstep.

The medical syringe pump according to the present disclosure comprises a syringe receptacle for receiving a syringe comprising a syringe cylinder and a plunger movable therein between a first end position and a second end position, wherein the plunger is connected to a plunger rod.

Further, the medical syringe pump according to the present disclosure comprises a syringe motor and a slide movable by the syringe motor in motor steps being in particular distinguishable or definable from each other. The slide comprises a toggle for receiving a section of the plunger rod of the syringe or for connecting the toggle thereto. This section may be a push plate which is connected to the plunger rod. The toggle is arranged to be movable by the slide relative to the syringe receptacle maximally between a first end stop and a second end stop. The slide is configured to be moved in motor steps (could be microsteps). This occurs longitudinally to the position of a syringe being inserted in the syringe pump during use of the latter.

Further, the medical syringe pump according to the present disclosure to be calibrated comprises a counting device for counting the number of motor steps by which the slide is moved, e.g. similar to an odometer which may preferably count back and forth and which may also preferably be set to zero or another start value.

In addition, the medical syringe pump according to the present disclosure comprises a first sensor and a second sensor, both of which are arranged along a shifting path of the plunger of the syringe or along a movement path of the slide of the pump. They are optionally configured and/or arranged to be in sensor relationship with the slide or with a section thereof.

Moreover, the syringe pump comprises a control device which is configured to move the slide by following control instructions. These control instructions may for example be entered by a user using an input device and/or stored by a storage device and read out from the latter.

For this purpose and possibly for storing the data detected by the sensors or the calculated calibration values, the syringe pump comprises a storage device.

Finally, an input device for entering control instructions and/or other data by the user is also provided.

The control device of the medical syringe pump according to the present disclosure is configured and/or prepared to execute the method according to the present disclosure or to execute a method for calibrating the medical syringe pump which method encompasses one or more of the following steps:

a) The optional input of at least one piece of information about a specific type of the syringe. The input or entry may be made by the input device. This input may be made e.g. using a selection list for the user, for instance in the form of a menu field, a touch screen field (e.g. of the syringe pump or of a blood treatment apparatus e.g. according to the present disclosure being connected to the syringe pump in signal communication) etc. Said selection may be carried out e.g. via the service menu. Advantageously, there is no need for the service technician to be present on site for this purpose. This input may be followed by a saving of this information by the storage device.

b) Moving a section of the slide in a, for example, middle position between the first end position and the second end position, in particular in a position between the first and the second sensor, however as long as this position is not reached yet. This takes place particularly at a first speed.

c) Moving the toggle by the slide such that the plunger, when the syringe is inserted in the syringe pump, would reach or come into the first end position or until a predetermined section of the slide, e.g. the permanent magnet, reaches the first end stop. This takes place particularly at a second speed. Hereby, when a predetermined section of the slide, e.g. a permanent magnet, reaches or passes by the position of the second sensor, this position is set or determined as a first counting value or is set equal thereto. This is, for example, the case precisely when the permanent magnet passes the second sensor exemplarily designed as a Hall sensor, or when a light barrier which corresponds to the second sensor is interrupted by the predetermined section. This first count value may be e.g. a number of motor steps provided by the counting device. Possibly, the first count value is, optionally temporarily, stored. Further, when the plunger reaches the first end position or the section of the slide reaches the first end stop then the motor steps, which have been counted by the counting device until reaching or having reached the position of the first end position or of the first end stop, are set or determined as a second count value. This value is also optionally, e.g. temporarily, stored.

d) Calculating a calibration value of the second sensor based on the first count value and the second count value, e.g. as a difference between, or the sum of, the first count value and the second count value, or as the absolute value therefrom, said calculation being done, e.g., by a calculation device suitable therefor or by the counting device, and storing of this calibration value for the second sensor by the storage device.

e) Optionally, the counting device is reset to "0" or to another start value.

f) Moving the toggle or the slide, in particular at the second or at a third speed, towards the second end position.

g) Determining the number of motor steps as third count value which number of motor steps is given or output by the counting device when the predetermined section of the slide has reached the position of the first sensor or has passed it by (e.g. the permanent magnet passing by a Hall sensor, or the passing of a light barrier).

h) Calculating a calibration value of the first sensor based on the third count value and optionally based on at least a further value from the group consisting of the first count value, the second count value and the calibration value of the second sensor, e.g. as the difference between the second and the third count value or as the absolute value of the third count value, said calculation being done by e.g. a therefor suitable calculation device or by the counting device, and storing this calibration value for the first sensor by the storage device.

The blood treatment apparatus according to the present disclosure comprises, and/or is connected in signal communication to, a medical syringe pump according to the present disclosure and/or a syringe pump which has been calibrated by the method according to the present disclosure.

A digital, in particular non-volatile, storage medium according to the present disclosure, in particular in the form of a machine-readable carrier, in particular in the form of a floppy disk, CD, DVD or an EPROM, in particular with electronically or optically readable control signals, can interact with a programmable computer system such that the machine-induced steps of the method according to the disclosure are prompted.

A computer program product according to the present disclosure comprises a program code volatile or saved on a machine-readable carrier or a signal wave for prompting the machine-induced steps of the method according to the disclosure when the computer program product runs on a computer. A computer program product can according to the present disclosure be understood as, for example, a computer program which is stored on a carrier, an embedded system as a comprehensive system with a computer program (for example, an electronic device with a computer program), a network of computer-implemented computer programs (for example, a client-server system, a cloud computing system, etc.) or a computer on which a computer program is loaded, running, saved, executed or developed.

The term "machine-readable carrier", as used herein, denotes in certain exemplary embodiments according to the present disclosure a carrier containing data or information, which is interpretable by software and/or hardware. The carrier may be a data carrier such as a floppy disk, a CD, DVD, a USB stick, a flashcard, an SD card or the like.

A computer program according to the present disclosure comprises a program code for prompting the machine-induced steps of the method according to the present disclosure when the computer program runs on a computer. According to the disclosure, a computer program can be understood as, for example, a physical, ready-for-distribution software product, which comprises a program.

It is applicable for the digital storage medium according to the present disclosure, the computer program product according to the present disclosure and the computer program according to the present disclosure that all, several or some of the machine-induced steps of the method according to the present disclosure are prompted. This applies particularly in interaction with a detecting device and/or with a blood treatment apparatus according to the present disclosure as described herein.

Embodiments according to the present disclosure may comprise one or several of the features mentioned above or in the following. In this, the features mentioned herein may, in any arbitrary combination, be subject-matter of embodiments according to the present disclosure, unless the person skilled in the art recognizes a specific combination as technically impossible.

Whenever an embodiment is mentioned herein, it is then an exemplary embodiment according to the present disclosure.

In several embodiments, to proceed according to step b) the section of the slide is first moved towards the first end stop, and is subsequently further moved, particularly at a second speed, after either the section or the predetermined section, e.g. the permanent magnet, has reached either the position of the second sensor or of the first end stop. In this, after the position of the second sensor or of the first end stop has been reached, the section of the slide is automatically moved by a predetermined number of motor steps or microsteps towards the second end stop, prior to being subsequently further moved according to step c).

In some embodiments, the toggle or the section reaches it maximal positions when the slide reaches the first end stop or the second end stop, respectively.

Recognizing that the first or the second end stop is reached may be done by a slotted disc or perforated disc which is optionally part of the syringe pump according to the present disclosure or part of the syringe pump to be calibrated. Said slotted disc may be driven, e.g. via coupling, by the spindle of the syringe pump which in connection with the pump motor drives also the slide in motor steps. The slotted disc intermittently breaks a light barrier signal when it turns, e.g. according to a known pattern. If the slotted disc stops, since the spindle which drives the slotted disc stops in turn when it reaches its mechanical end position, then the light barrier signal remains static or deviates in another way from the pattern previously known or expected for a movement state of the slide. The control device of the syringe pump may hereby detect the stoppage of the slotted disc and hereby detect in turn the stoppage of the spindle and consequently of the slide. Thus, one of the end stops is arrived, i.e. reached.

In some embodiments, the syringe is a disposable.

The movement and the stoppage of the spindle may be detected using different working sensors, for instance a magnet field sensor, like Hall sensors, instead of using a light barrier or another optical sensor.

Instead of using optical sensors and/or magnet field sensors, for example, at least a resistance track may be used which functions with loop and resistance track according to the principle of a potentiometer.

In several embodiments, the first speed is higher than the second speed and/or higher than the third speed.

In some embodiments, the third speed is higher than the second speed. In others, it is as high as the second speed.

In several embodiments, at least a determined number of motor steps and/or at least a count value is offset with a compensation value and therefore is entered corrected or compensated in the calculation of the calibration values of the first sensor and/or the second sensor according to steps d) and g).

An exemplary compensation may look like the following: Reaching the end stop is exemplarily determined based on the time out or the change of the slotted disc signal expected for a continuous movement of the slide.

The time out is obviously dependent on the speed at which the slide is moved during calibration: if moved fast, for instance at the first speed, then a stoppage of the slide is expected at or with a time out which lasts e.g. more than at least 750 ms. If moved at the second speed, then a stoppage of the slide is expected at or with a time out which lasts e.g. more than at least 1500 ms. If it moves slowly, for instance at the third speed, then a stoppage of the slide is expected at or with a time which lasts e.g. more than at least 3750 ms.

This means that reaching the end stop may only belated be reliably detected. This leads to a deviation in the position detection which deviation is different depending on the speed.

In order to eliminate the error caused therethrough, a compensation value which may depend on the speed has been experimentally determined. The determined count values, sensor positions or calibration values may be corrected by such compensation values.

In some embodiments, the calibration values of the first sensor and/or of the second sensor are checked for plausibility after having been corrected or compensated as described above.

In several embodiments, the first sensor and/or the second sensor is a Hall sensor or another magnet field sensor, or a light barrier or another optoelectronic sensor. Instead of using optical sensors and/or magnet field sensors, for example at least a resistance track may be used which functions with loop and resistance track according to the principle of a potentiometer.

In some embodiments, the slide of the syringe pump comprises a permanent magnet. The latter is in a constant distance to the toggle or to the aforementioned section of the slide.

In certain embodiments, the information about the particular syringe type includes at least the distance between the first and the second end position of the syringe.

In some embodiments, the medical syringe pump is designed as heparin syringe pump.

In certain embodiments, the blood treatment apparatus is designed as a peritoneal dialysis apparatus, hemodialysis apparatus, hemofiltration apparatus or as hemodiafiltration apparatus, in particular as an apparatus for the chronic renal replacement therapy or the continuous renal replacement therapy (CRRT).

In several embodiments, the predetermined section is the position of the permanent magnet on the slide.

In some embodiments, the sensors, in particular designed as Hall sensors, and/or their line connection are not detached from the control device during or for calibration.

In several embodiments, the positions of the sensors, in particular designed as Hall sensors, are not changed during or for calibration. Their relative position to other sections of the syringe pump, for instance its housing, remains unchanged.

In some embodiments, the syringe is received in the syringe receptacle during or for calibration.

In several embodiments, the medical syringe pump comprises no pressure sensors.

In some embodiments, the control device and/or the syringe pump comprises no pressure valve and is also not connected to same, in particular not electrically.

In several embodiments, the control device and/or the syringe pump comprises no pressure detection unit and/or pressure measuring unit and is also not connected to same, in particular not electrically.

In some embodiments, the method according to the present disclosure encompasses no pressure testing mechanism.

In several embodiments, no pressure data and/or electrical voltage data are measured, detected, compared or processed in another way in the method according to the present disclosure.

Some or all embodiments according to the present disclosure may comprise one, several or all of the aforementioned and/or the following advantages.

With the aid of the method according to the present disclosure, the sensors of the syringe pump can be calibrated in a simple and fast manner. This saves time and effort.

By moving the slide during calibration at different speeds, time may be saved in that, on the one hand the slide is moved as fast as possible which may shorten the calibration. At the same time, in other moments of the calibration the movement is performed or executed as slowly as necessary to ensure the required precision, for instance when arriving at positions which are critical for the calibration. This change between different speeds of the slide during or upon calibration thus represents a further advantage.

Advantageously, installation-related deviations in the positions of the sensors and mechanical tolerances, for example the sensor signal width, are taken into account in the calibration according to the present disclosure. The automatic calibration saves a complex or burdensome adjustment by hand.

Particular precision in the factory mounting of the sensors is not required according to the present disclosure. Mounting clearances are permissible and may become less important through or by the method according to the present disclosure.

BRIEF DESCRIPTION OF THE FIGURES

The present disclosure is exemplarily explained below with regard to the accompanying drawings in which identical reference numerals refer to the same or similar components. In the figures, the following applies:

FIG. 4 shows the execution of an exemplary embodiment of the method according to the present disclosure in a summary.

DETAILED DESCRIPTION

Figures 1A, 1B:
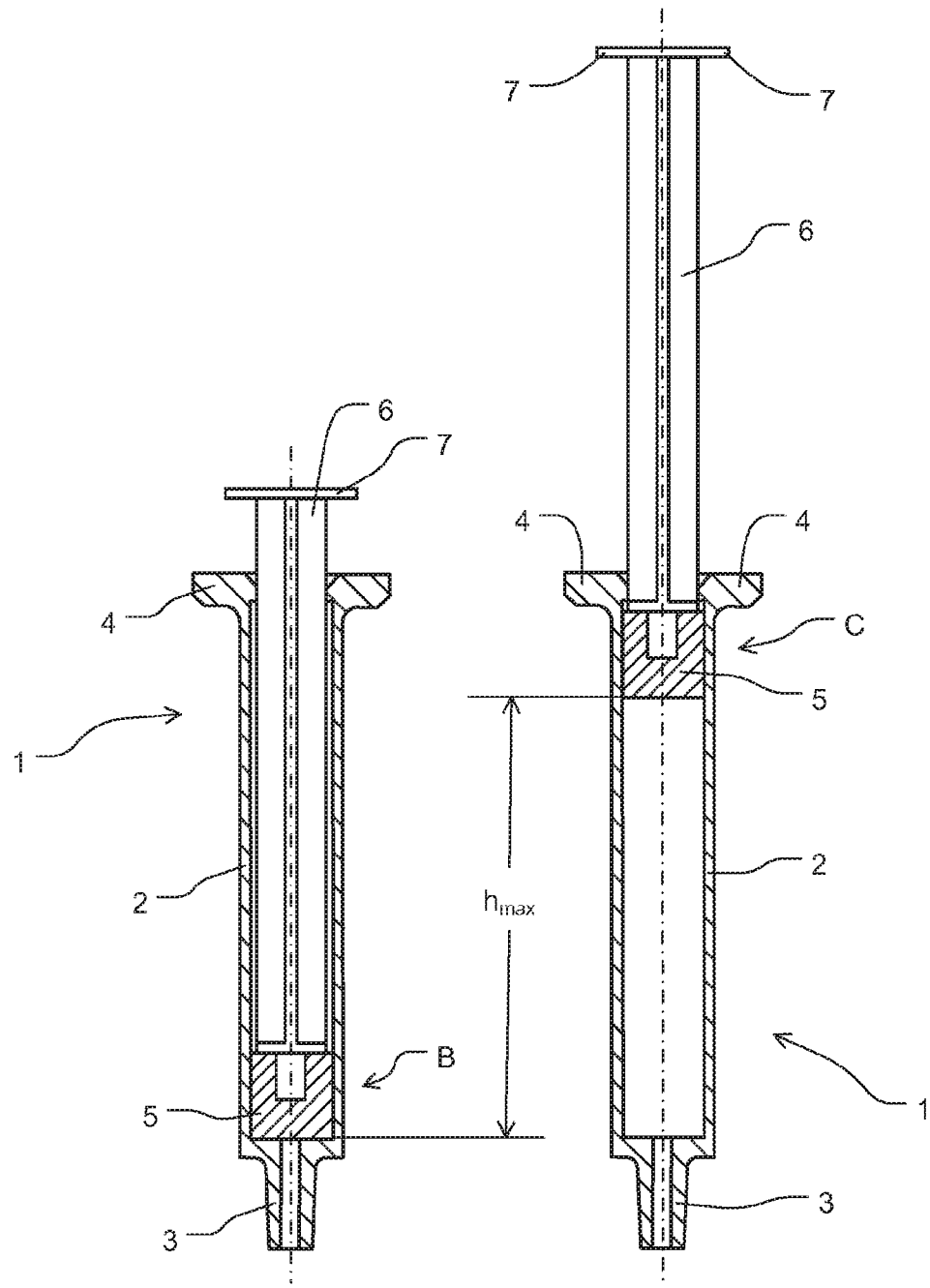
FIG. 1 shows a conventional syringe.

FIG. 1a and FIG. 1b show, each from the side, a conventional syringe 1, e.g. fillable with heparin, which may be a disposable syringe and/or a pre-filled syringe. FIG. 1a shows said syringe in an empty state, FIG. 1b shows it in a completely filled state or the state it takes when it is completely filled.

The syringe 1 comprises a syringe cylinder 2 and a plunger 5.

The syringe cylinder 2 comprises an optional luer cone 3 integrally formed on its head side and a syringe flange 4 formed on the opposite end.

The plunger 5 is usually made of elastomer material and is plug-shaped. It is positioned in the interior of the syringe cylinder 2 and is connected to a plunger rod 6 enabling it to be axially movable within the syringe cylinder 2.

The plunger 5 ends with a usually oval or round push plate 7 when viewed from the top. The push plate 7 is shown from the side in FIG. 1a and FIG. 1b.

In FIG. 1a, the plunger 5 is in a first end position B, in FIG. 1b in a second end position C. The plunger 5 arrives at or assumes the first end position B when the syringe content is completely emptied by moving the plunger 5. The plunger 5 arrives at the second end position C when the syringe 1 is filled to the maximum.

The shifting path of the plunger 5 within the syringe 1 is thus limited by both end positions B and C. The maximum displacement path to be maintained when the syringe 1 is used as intended is herein referred to as $h_{max}$ which is not to be exceeded in order to prevent the plunger 5 from being pulled out of the syringe cylinder 2 and the possible contamination risk associated therewith.

Figure 2:
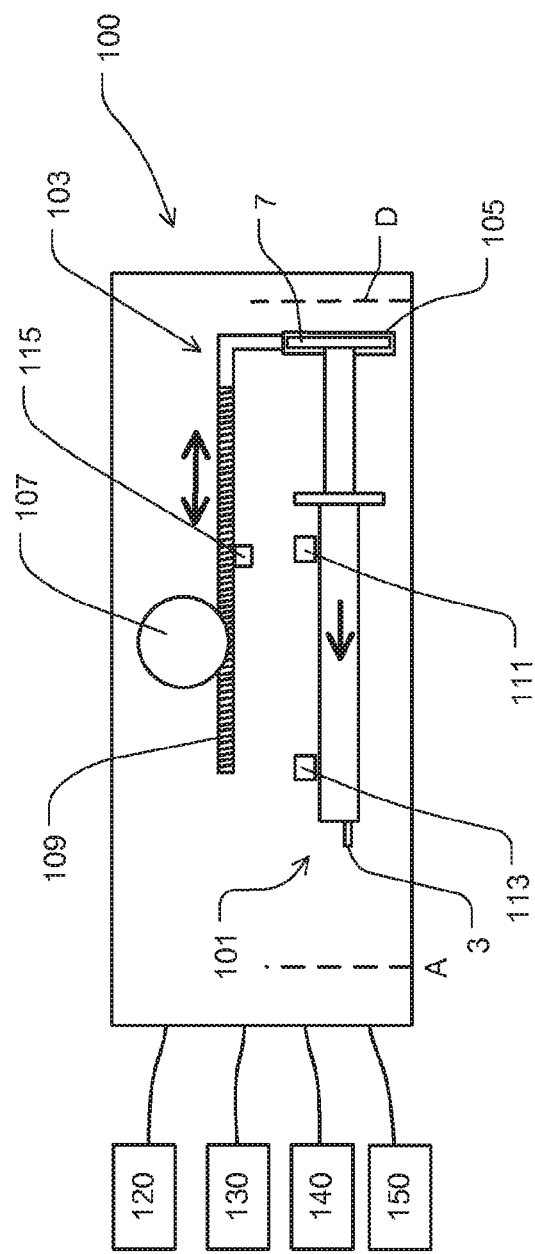
FIG. 2 shows an embodiment of the syringe pump according to the present disclosure in a schematically simplified top view.

FIG. 2 shows an embodiment of a syringe pump 100 according to the present disclosure comprising a syringe receptacle with a syringe cavity 101. It further comprises a movable slide 103 having a toggle 105 being movable together with said slide 103, wherein the toggle 105 is fixed stationary or integrally relative to the slide or is a stationary or integral part thereof.

A motor 107 moves, e.g. via a spindle 109, the slide 103 in motor steps. The direction in which the travel or movement path of the slide 103 extends is indicated by double arrow.

The movement of the slide 103 comes leftwards (with regard to FIG. 2), i.e. towards the luer cone 3, to a halt or standstill latest when a first end stop A is reached, which is indicated by a dashed line.

The movement of the slide 103 comes rightwards (with regard to FIG. 2), i.e. towards the push plate 7, to a halt latest when a second end stop D is reached, which is likewise indicated by a dashed line.

The end stops A and D are to be understood as mechanical final stops of the slide 103: moving the slide over or beyond these points A and D is technically impossible, even when no syringe 1 is inserted in the syringe pump 100.

The end stops A and D are each outside the first and second end position B respectively C, described with regard to FIG. 1.

At the syringe receptacle, a first sensor 111 and a second sensor 113 are stationary connected to e.g. a housing of the syringe pump 100.

The slide 103 in turn may comprise a permanent magnet 115 which may serve to detect, in known manner, in interaction or alternation with the first sensor 111 and/or the second sensor 113, when the slide 103 reaches the position of the first sensor 111 or of the second sensor 113 or passes by. The first and the second sensor 111 or 113 are therefore configured as Hall sensors. Evaluation devices required for determining or evaluating the signals received from the Hall sensors are provided.

As an alternative to configuring the sensors 111 and 113 as Hall sensors, one or both sensors may be designed as light barriers, wherein combinations of a Hall sensor and a light barrier are likewise contemplated by the present disclosure.

Further contemplated by the present disclosure is that both sensors 111 and 113, or any one of them, being stationary with the slide 103, move together with the slide 103 when it is being moved. In such embodiments, the permanent magnet 115 may be positioned at the syringe receptacle.

The syringe pump 100 further comprises a counting device 120, a control device 130, a storage device 140 and an input device 150 or is respectively connected thereto in signal communication, as indicated in FIG. 2.

FIG. 2 shows the syringe pump 100 according to the present disclosure having a syringe 1 inserted therein. This shared or joint illustration serves for a better explanation of the interaction of the syringe pump 100 and the syringe 1 during the intended use of the syringe pump 100 or the syringe 1. It is however not required to insert the syringe 1 in the syringe pump 100 for calibrating.

For the experimental determination of the offset for the automatic calibration process, the reference syringe was previously inserted in several syringe pumps of the same type and the average value detected therefrom has been stored in the storage device. This process for determining the offset is not part of the intended use of the syringe pump. For calibration however, the offset according to step a) may be stored or entered or accordingly read out.

Figure 3:
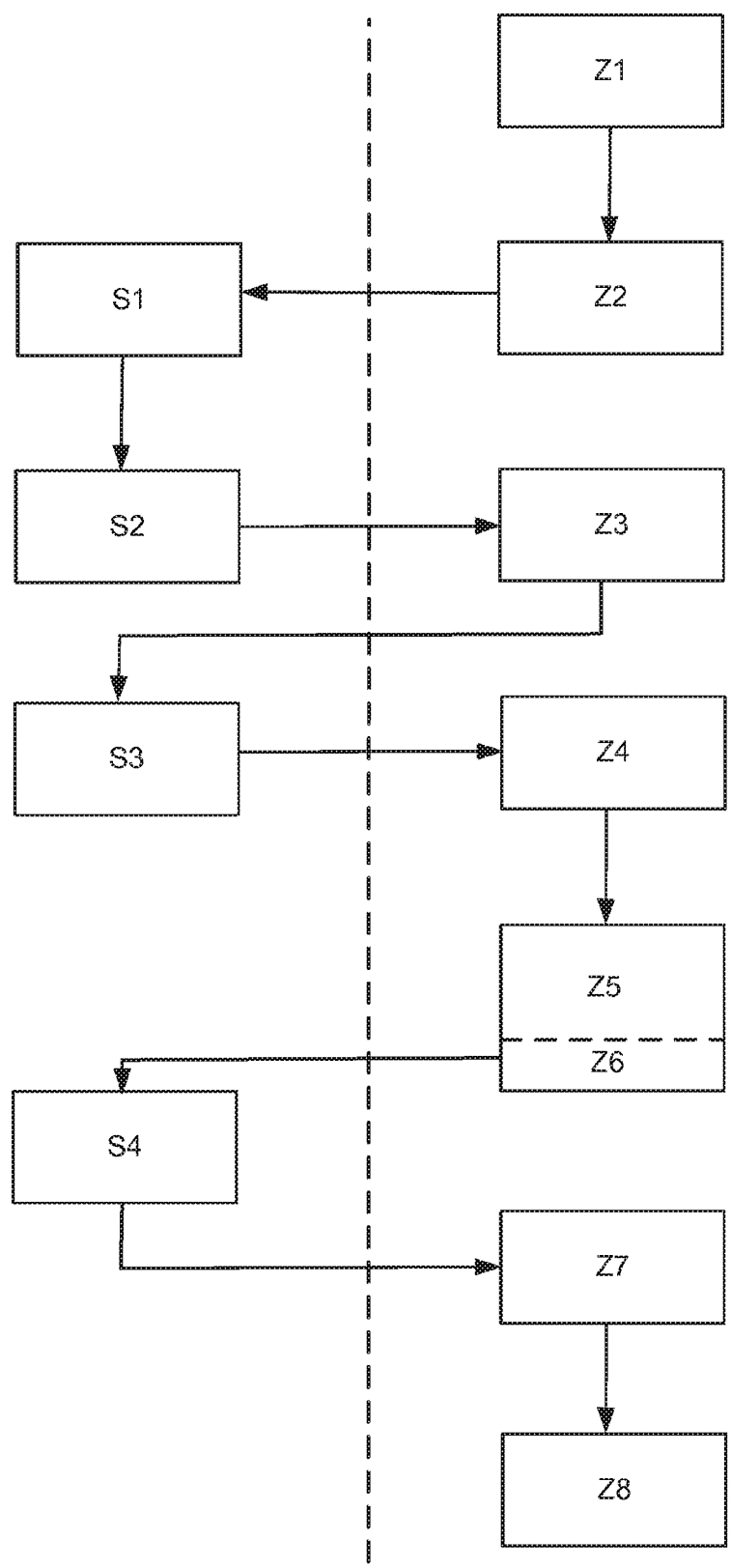
FIG. 3 shows the execution of an exemplary embodiment of the method according to the present disclosure in a flow diagram.

FIG. 3 shows the execution of an embodiment of the method according to the present disclosure in a flow diagram, wherein the steps denoted with "S" refer to steps of the syringe pump 100 relating to the slide and the steps denoted with "Z" refer to steps relating to the input device 150 (or by the latter), the counting device 120 or the storage device 140. The following applies:

Step Z1 is optional and relates to entering at least information about a particular type of the syringe 1 using the input device 150. The above offset may be included thereto.

Step Z2 is likewise optional and relates to reading out the information about a particular type of the syringe 1 (e.g. $h_{max}$) stored in the storage device 140.

Step S1 relates to moving the toggle 105 by the slide 103 in a position between the first end position B and the second end position C, in particular in a position between the first sensor 111 and the second sensor 113, in case this position has not been already reached. This may take place in particular at a first speed. This may be between 100 μs/microstep and 1000 μs/microstep, preferably 500 μs/microstep.

A microstep is a step size of the pump motor; the term may stand for a rotation measure or for a linear measure.

Step S2 relates to moving the toggle 105, particularly at a second speed, by the slide 103 such that the plunger with an inserted syringe would reach the first end position B or until a predetermined section of the slide 103, e.g. the permanent magnet 115 has reached the first end stop A. Said second speed may be between 1000 μs/microstep and 10000 μs/microstep, preferably 5000 μs/microstep. Alternatively, the second speed may be between 1000 μs/microstep and 2000 μs/microstep, in particular 1400 μs/microstep.

When the predetermined section of the slide 103, e.g. the permanent magnet 115, reaches or passes by the position of the second sensor 113 according to step Z3, the motor steps, upon or when reaching or passing by this position, are set or determined, e.g. by the counting device 120, as a first count value ZW1 and are stored as position of the second sensor 113. Optionally, the counting device 120 is reset to "0" afterwards.

In step S3 the toggle 105 is moved by the slide 103 further on towards the first end position B or the second end stop A.

Hence, in step Z4 when the plunger 5 reaches the first end position B or when the slide 103 reaches the first end stop A, a second count value ZW2 detected by the counting device 120 is determined. This may be stored as position of the end position B or as position of the end stop A.

Step Z5 relates to calculating, e.g. using the counting device 120 or another device programmed for this purpose, a calibration value K2 of the second sensor 113 based on both previous count values ZW1 and ZW2. This calibration value K2 for the second senor 113 is stored by the storage device 140.

Step Z6 is optional and relates to resetting the counting device 120, e.g. to "0".

In step S4 the toggle 105 is moved by the slide 103, in particular at the a.m. second speed or at a third speed, towards the second end position C. The third speed may be between 10000 µs/microstep and 50000 µs/microstep, preferably 20000 µs/microstep.

Step Z7 relates to detecting or determining the position of the first sensor 111 by the counting device 120. Said position is determined starting from the first end position B or from the first end stop A until the predetermined section of the slide 103, e.g. the permanent magnet 115, reaches or passes by the position of the first sensor 111, by a third count value ZW3 which is optionally stored e.g. as position of the first sensor 111.

In step Z8 a calibration value K1 for the first sensor 111, is now determined for example based on the set value ZW3. In some embodiments this calibration value K1 may be calculated additionally with reference to the already set and stored lengths and/or positions. This calibration value K1 for the first sensor 111 is likewise stored by the storage device 140.

FIG. 4 shows the execution of an exemplary embodiment of the method according to the present disclosure in a summary.

The summary further illustrates the set count values ZW1, ZW2 and ZW3. Said values are each set or determined when the here exemplary permanent magnet 115 reaches and/or passes the sensor 111, 113 in the direction indicated by the respective arrow or when the first end position A is reached. These count values ZW1, ZW2 and ZW3 may be used for determining the calibration values K1 and K2, which specify the position of the Hall sensors relative to the first end stop A (or relative to the first end position B).

Alternatively, it is possible to set the counting device 120 to zero upon or when reaching the respective positions and thus to directly consider or accept the determined count values as calibration values.

LIST OF REFERENCE NUMERALS 1 syringe
2 syringe cylinder
3 luer cone
4 syringe flange
5 plunger
6 plunger rod
7 press plate
100 syringe pump
101 syringe cavity
103 slide
105 toggle or pin
107 motor
109 spindle
111 first sensor
113 second sensor
115 permanent magnet
120 counting device
130 control device
140 storage device
150 input device
A first end stop
B first end position
C second end position
D second end stop
Sx $n^{th}$ method step on the syringe pump side
Zx $n^{th}$ method step on the side of the input device, storage device or counting device
K1 calibration value of the first sensor 111
K2 calibration value of the second sensor 113
ZW1 first count value
ZW2 second count value
ZW3 third count value
$h_{max}$ maximum displacement of the plunger or of the plunger rod inside the syringe cylinder when the syringe is used as intended; the maximum displacement is determined such that an undesirable pulling or withdrawal of the plunger out of the cylinder is avoided

The invention claimed is:

1. A method for calibrating a medical syringe pump, the syringe pump comprising:
a syringe receptacle configured to receive a syringe comprising a syringe cylinder and a plunger that is movable within the syringe cylinder between a first end position and a second end position, wherein the plunger is connected to a plunger rod;
a slide movable in motor steps and having a toggle for receiving a section of the plunger rod or for connecting thereto, wherein a section of the slide is arranged to be movable maximally between a first end stop and a second end stop relative to the syringe receptacle, and wherein the syringe pump is configured to move the slide in motor steps;
a counting device for counting the number of motor steps by which the slide is being moved;
a first sensor and a second sensor, both arranged along a shifting path of the plunger or along a travel or movement path of the slide;
a control device configured for moving the slide according to control instructions;
a storage device; and
an input device for entering control instructions and/or other data by a user,
wherein the method for calibrating the syringe pump comprises:
a) moving, at a first speed, a section of the slide to a position between the first sensor and the second sensor;
b) moving, at a second speed, the toggle by the slide such that the plunger, when a syringe is inserted, would reach or come to a first end position, or until a predetermined section of the slide, reaches the first end stop,
wherein, when the predetermined section of the slide reaches or passes by the position of the second sensor, the number of motor steps given or output for or at this position by the counting device is determined as a first count value, and wherein, when the plunger reaches the first end position or when the section of the slide reaches the first end stop, the motor steps, which have been counted by the counting device until reaching the position of the first end position or of the first end stop are determined as a second count value;
c) calculating a calibration value for the second sensor based on the first count value and the second count value;
d) storing, by the storage device, the calibration value for the second sensor;
e) moving the toggle at the second or a third speed towards the second end position;
f) determining the number of motor steps output by the counting device as a third count value upon reaching the position of the first sensor or passing it by the predetermined section of the slide;
g) calculating a calibration value for the first sensor based on the third count value; and
h) storing, by the storage device, the calibration value for the first sensor.

2. The method of claim 1, further comprising entering at least information about a particular type of the syringe using the input device and storing this information by the storage device.

3. The method of claim 1, further comprising resetting the counting device to zero or to a predetermined start value or number.

4. The method of claim 1, wherein the calculating the calibration value for the first sensor is also based on a further value from the group consisting of: the first count value, the second count value, and the calibration value of the second sensor.

5. The method according to claim 1, wherein to proceed according to step a) the section of the slide is first moved towards the first end stop, and wherein moving the section of the slide at the second speed continues after either the position of the second sensor or the first end stop is reached,
wherein, after the position of the second sensor or of the first end stop has been reached, the section of the slide is automatically moved by a predetermined number of motor steps towards the second end stop, prior to being subsequently further moved according to step b).

6. The method according to claim 1, wherein the first speed is higher than the second speed and/or than the third speed.

7. The method according to claim 1, wherein the third speed is higher than or identical to the second speed.

8. The method according to claim 1, wherein the determined number of motor steps is offset with a compensation value and therefore is entered or included compensated in the calculation of the calibration values of the first sensor and/or the second sensor according to steps c) and g).

9. The method according to claim 1, wherein the corrected calibration values of the first sensor and/or of the second sensor are verified or checked for plausibility.

10. The method according to claim 1, wherein the first sensor and/or the second sensor is a magnet field sensor, an optoelectronic sensor, and/or part of a resistance trail or path which functions according to the principle of a potentiometers.

11. The method according to claim 1, wherein the slide comprises a permanent magnet being movable to the section of the slide in a constant distance.

12. The method according to claim 2, wherein the information about the particular syringe type includes at least the distance between the first end position and the second end position and/or a correction factor and/or an offset.

13. The method according to claim 1, wherein the predetermined section of the slide includes a permanent magnet, and wherein the moving, at the second speed, the toggle by the slide is performed until the permanent magnet reaches the first end stop.

14. A digital storage medium with electronically readable control signals configured to interact with a programmable computer system such that the machine-induced steps of a method according to claim 1 are prompted.

15. The digital storage medium of claim 14, wherein the digital storage medium comprises a floppy disk, a CD, a DVD, or an EPROM.

16. A computer program product, as a signal wave or program code stored on a machine-readable storage medium, for prompting the machine-induced steps of the method according to claim 1, when the computer program product runs on a computer.

17. The computer program product of claim 16, wherein the computer program product comprises the program code stored on the machine-readable storage medium.

18. A medical syringe pump, comprising
a syringe receptacle configured to receive a syringe comprising a syringe cylinder and a plunger that is movable within the syringe cylinder between a first end position and a second end position, wherein the plunger is connected to a plunger rod;
a slide movable in motor steps and having a toggle for receiving a section of the plunger rod or for connecting thereto, wherein a section of the slide is arranged to be movable maximally between a first end stop and a second end stop relative to the syringe receptacle, and wherein the syringe pump is configured to move the slide in motor steps;
a counting device for counting the number of motor steps by which the slide is being moved;
a first sensor and a second sensor, both arranged along a shifting path of the plunger or along a travel or movement path of the slide;
a control device configured for moving the slide according to control instructions;
a storage device; and
an input device for entering control instructions and/or other data by a user,
wherein the control device is configured to execute a calibration method comprising:
a) moving, at a first speed, a section of the slide to a position between the first sensor and the second sensor;
b) moving, at a second speed, the toggle by the slide such that the plunger, when a syringe is inserted, would reach or come to a first end position, or until a predetermined section of the slide, reaches the first end stop,
wherein, when the predetermined section of the slide reaches or passes by the position of the second sensor, the number of motor steps given or output for or at this position by the counting device is determined as a first count value, and
wherein, when the plunger reaches the first end position or when the section of the slide reaches the first end stop, the motor steps, which have been counted by the counting device until reaching the position of the first end position or of the first end stop are determined as a second count value;

c) calculating a calibration value for the second sensor based on the first count value and the second count value;
d) storing, by the storage device, the calibration value for the second sensor;
e) moving the toggle at the second or a third speed towards the second end position;
f) determining the number of motor steps output by the counting device as a third count value upon reaching the position of the first sensor or passing it by the predetermined section of the slide;
g) calculating a calibration value for the first sensor based on the third count value; and
h) storing, by the storage device, the calibration value for the first sensor.

19. The syringe pump of claim 18, wherein the calibration method further comprises:
entering information about a particular type of the syringe using the input device; and
storing the information about the particular type of the syringe by the storage device.

20. The syringe pump of claim 18, wherein the calibration method further comprises resetting the counting device to zero or to a predetermined start value or number.

21. The syringe pump of claim 18, wherein the calculating the calibration value for the first sensor is also based on a further value from the group consisting of: the first count value, the second count value, and the calibration value of the second sensor.

22. The syringe pump of claim 18, wherein to proceed according to step a) the section of the slide is first moved towards the first end stop, and moving the section of the slide at the second speed continues after either the position of the second sensor or of the first end stop is reached,
wherein, after the position of the second sensor or of the first end stop has been reached, the section of the slide is automatically moved by a predetermined number of motor steps towards the second end stop, prior to being subsequently further moved according to step b).

23. The syringe pump of claim 18, wherein the first speed is higher than the second speed and/or than the third speed.

24. The syringe pump of claim 18, wherein the third speed is higher than or identical to the second speed.

25. The syringe pump of claim 18, wherein the determined number of motor steps is offset with a compensation value and therefore is entered compensated in the calculation of the calibration values of the first sensor and/or the second sensor according to step c) and g).

26. The syringe pump of claim 18, wherein the thus corrected calibration values of the first sensor and/or of the second sensor are verified or checked for plausibility.

27. The syringe pump of claim 18, wherein the first sensor and/or the second sensor is a magnet field sensor or an optoelectronic sensor.

28. The syringe pump of claim 18, wherein the slide comprises a permanent magnet being movable in a constant distance to the section of the slide.

29. The syringe pump of claim 18, wherein the information about the particular syringe type includes at least the distance between the first end position and the second end position and/or a correction factor and/or an offset.

30. The syringe pump of claim 18, wherein the syringe pump comprises a heparin syringe pump.

31. The syringe pump of claim 18, wherein the syringe pump is calibrated according to steps a) through h) of the calibration method.

32. The syringe pump of claim 31, wherein the predetermined section of the slide includes a permanent magnet, and wherein the moving, at the second speed, the toggle by the slide is performed until the permanent magnet reaches the first end stop.

33. A blood treatment apparatus comprising, or being connected in signal communication to, the medical syringe pump of claim 18.

34. The blood treatment apparatus according to claim 33, designed as a peritoneal dialysis apparatus, a hemodialysis apparatus, a hemofiltration apparatus, a hemodiafiltration apparatus, or an apparatus for chronic renal replacement therapy or continuous renal replacement therapy.

* * * * *